United States Patent [19]

Kaper et al.

[11] Patent Number: 5,399,494

[45] Date of Patent: * Mar. 21, 1995

[54] VIBRIO CHOLERAE STRAIN CVD103HG$^r$, METHOD OF MAKING SAME, AND VACCINES DERIVED THEREFROM

[75] Inventors: James B. Kaper; Myron M. Levine, both of Columbia, Md.

[73] Assignee: The University of Maryland System, Baltimore, Md.

[ * ] Notice: The portion of the term of this patent subsequent to Jun. 19, 2007 has been disclaimed.

[21] Appl. No.: 936,829

[22] Filed: Aug. 28, 1992

Related U.S. Application Data

[63] Continuation-in-part of Ser. No. 757,930, Sep. 12, 1991, abandoned, which is a continuation of Ser. No. 581,406, Feb. 17, 1984, Pat. No. 5,135,862, which is a continuation-in-part of Ser. No. 472,276, Mar. 4, 1983, abandoned.

[51] Int. Cl.$^6$ .................. C12N 1/21; C12N 15/03; C12N 15/31; C12R 1/63
[52] U.S. Cl. .................. 435/172.3; 435/317.1; 435/909; 536/23.7; 935/56; 935/72; 935/84
[58] Field of Search ............... 435/172.1, 172.3, 252.3, 435/320.1, 909, 252.3, 317.1; 424/93 A, 92, 93.48; 536/23.7; 935/29, 52, 56, 72, 84

[56] References Cited

U.S. PATENT DOCUMENTS

| | | | |
|---|---|---|---|
| 4,264,737 | 4/1981 | Murphy | 435/172.1 |
| 4,666,837 | 5/1987 | Harford et al. | 435/69.3 |
| 4,882,278 | 11/1989 | Mekalanos | 435/172.3 |

FOREIGN PATENT DOCUMENTS

| | | |
|---|---|---|
| 0018154 | 10/1980 | European Pat. Off. . |
| 0095452 | 11/1983 | European Pat. Off. . |
| 0119031 | 9/1984 | European Pat. Off. . |
| 2436818 | 8/1980 | France . |
| 2032955 | 5/1980 | United Kingdom . |

OTHER PUBLICATIONS

Yokota, T. et al., "Genetic Behavior of R Factors in *Vibrio cholerae*", *J. of Bacteriology*, vol. 109, Jan. 1972. pp. 440–442.

Cuatrecasas, P., "*Vibrio cholerae* Choleragenoid. Mechanism of Inhibition of Cholera Toxin Action", *Biochemistry*, 12, No. 18, 1973, pp. 3577–3581.

Cash, R. et al., "Response Of Man To Infection With *Vibrio cholerae* . . . ", *J. Of Infectious Disease*, vol. 129, No. 1, by Univ. of Chicago, Jan. 1974, pp. 45–52.

Finkelstein, R. et al., "Studies On Toxinogenesis In *Vibrio cholerae* . . . ", *J. Of Infectious Diseases*, vol. 129, No. 2, by Univ. of Chicago, Feb. 1974, pp. 117–123.

Guerrant, R. et al., "Cyclic Adenosine Monophosphate and Alteration of Chinese Hamster Ovary Cell Morphology . . . ", *Infection & Immunity*, vol. 10, No. 2, Aug. 1974, pp. 320–327.

Gill, D., "Involvement of Nicotinamide Adenine Dinucleotide in the Action of Cholera Toxin In Vitro", *Proc. Nat. Acad. Sci. USA*, vol. 72, No. 6, Jun. 1975, pp. 2064–2068.

Southern, E., "Detection of Specific Sequences Among DNA Fragments Separated by Gel Electrophoresis", *J. Mol.* 98, (1975), pp. 503–517.

(List continued on next page.)

*Primary Examiner*—Keith C. Furman
*Assistant Examiner*—Dian C. Jacobson
*Attorney, Agent, or Firm*—Bradford E. Kile

[57] ABSTRACT

Method of isolating deletion mutants of *Vibrio cholerae*, wherein the deletion is predetermined by digestion with restriction endonucleases of known specificity. The deletions are inserted into the *Vibrio cholerae* chromosome by in vivo recombination between a plasmid carrying the desired deletion, with adjacent flanking sequences, and the *Vibrio cholerae* chromosome. The invention includes the isolation and characterization of a new *Vibrio cholerae* strain, (ATCC No. 55456), having a deletion in the tox gene, as defined by Acc I, Xba I, Cla I and/or restriction endonuclease sites, and carrying a mercury resistance gene. The invention also includes vaccines for protecting against the symptoms of cholera as well as methods for achieving this protection.

8 Claims, 6 Drawing Sheets

OTHER PUBLICATIONS

Noriki, H., "Evaluation of Toxoid Field Trial In The Philippines", *Symposium on Cholera Sapporo*, 1976, pp. 302–310.

Levine, M., "Immunity to Cholera as Evaluated In Volunteers", *Cholera and Related Diarrheas*, 43rd Symp., Stockholm, 1978, pp. 195–203.

Beringer, J. et al., "Transfer Of The Drug-Resistance Transposon Tn5 to Rhizobium", *Nature*, vol. 276, Dec. 7, 1978, pp. 633–634.

Johnson, S. et al., "*Vibrio cholerae* Hybrid Sex Factor That Contains Ampicillin Transposon Tn1", *J. Of Bacteriology*, Jan. 1979, pp. 531, 536.

Honda, T. et al., "Selection And Characteristics Of A *Vibrio cholerae* Mutant . . . ", *Proc. Natl. Acad. Sci. USA*, vol. 76, No. 4, Apr. 1979, pp. 2052–2056.

Dallas, W. et al., "Cistrons Encoding *Escherichia coli* Heat-Labile Toxin", J. Of Bacteriology, vol. 139, No. 3, Sep. 1979, pp. 850–858.

Chilton, M. et al., "Tailoring The Agrobacterium Ti Plasmid As a Vector For Plant Genetic Engineering", *Stadler Symp.*, vol. 13, Univ. of Missouri, 1981, pp. 39–53.

Matzke, A. et al., "Site-Specific Insertion Of Genes Into T-DNA Of The Agrobacterium Tumor-Inducing Plasmid . . . ", *J. of Molecular and Applied Genetics*, vol. 1, No. 1, 1981, pp. 39–49.

Kaper, J. et al., "Molecular Characterization of Environmental and Nontoxigenic Strains of *Vibrio cholerae*", *Infection and Immunity*, vol. 32, No. 2, May 1981, pp. 661–667.

Sigel, S. et al., "Ability Of An Avirulent Mutant of *Vibrio cholerae* . . . ", *Infection and Immunity*, vol. 32, No. 2, May 1981, pp. 474–479.

Holmgren, J., "Actions Of Cholera Toxin And The Prevention And Treatment Of Cholera", *Nature*, vol. 292, Jul. 30, 1981, pp. 413–417.

Sublett, R. et al., "Transposon-Facilitated Recombination in Classical Biotypes Of *Vibrio cholerae*", *Infection and Immunity*, vol. 32, No. 3, Jun. 1981, pp. 1132–1138.

Thomson J. et al., "Mutagenesis By Insertion Of Drug Resistance Transposon Tn7 Into A Vibrio Species", *J. Of Bacteriology*, vol. 148, No. 1, Oct. 1981, pp. 374–378.

Baudry, B. et al., "Cloning Of a Gene (zot) Encoding A New Toxin Produced By *Vibrio cholerae*", *Infection & Immunity*, vol. 60, No. 2, Feb. 1992, pp. 428–434.

Levine, M. et al., "Volunteer Studies In Development Of Vaccines Against Cholera . . . ", *Acute Enteric Infections In Children*, Elsevier/North-Holland Biomedical Press, 1981, pp. 443–459.

Gennaro, M. et al., "The Expression Of Biologically Active Toxin In *Escherichia coli*", *Nucleic Acids Research*, vol. 10, No. 16, 1982, pp. 4283–4290.

Mekalanos, J. et al., "Isolation Of Enterotoxin Structural Gene Deletion Mutations In *Vibrio cholerae*", vol. 79, Jan. 1982, pp. 151–155.

Levine, M. et al., "Immunity Of Cholera In Man: Relative Role Of Antibacterial Versus Antitoxic Immunity", Transactions Royal Soc. Of Tropical Medicine & Hygiene, vol. 73, 1979, pp. 3–9.

Svennerholm, A. et al., "Intestinal Antibody Responses After Immunization With Cholera B. Subunit", *The Lancet*, Feb. 6, 1982, pp. 305–308.

Finkelstein, M. et al., "Protection In Rabbits Induced By The Texas Star-SR Attenuated $A^-B^+$ Mutant Candidate Live Oral Vaccine", Infection and Immunity, vol. 36, No. 1, Apr. 1982, pp. 221–226.

Pearson G. et al., "Molecular Cloning Of *Vibrio cholerae* Enterotoxin Genes In *Escherichia coli* K–12", *Proc. Natl. Acad. Sci. USA*, vol. 79, May 1982, pp. 2976–2980.

Lee, C. et al., "Use Of Cloned Intl Genes of *Escherichia coli* To Introduce mtl Deletion Mutations Into the Chromosome", J. Of Bacteriology, vol. 153, No. 2, Feb. 1983, pp. 685–592.

Mekalanos, J., "Duplication and Amplification Of Toxin Genes In *Vibrio cholerae*", *Cell*, vol. 35, Nove. 1983, pp. 253–263.

Lockman, H. et al., "Nucleotide Sequence Analysis Of The A2 and B Subunits Of *Vibrio cholerae* Enterotoxin", *J. Of Biological Chemistry*, vol. 258, No. 22, Nov. 1983, pp. 13722–13726.

Levine, M. et al., "New Knowledge On Pathogenesis Of Bacterial Enteric Infections As Applied To Vaccine Development", *Microbiological Reviews*, vol. 47, No. 4, Dec. 1983, pp. 510–550.

Mekalanos, J. et al., "Cholera Toxin Genes: Nucleotide Sequence, Deletion Analysis And Vaccine Development", *Nature*, vol. 306, Dec. 8, 1983, pp. 551–557.

Svennerholm, A. et al., "Local And Systemic Antibody Responses And Immunological Memory In Humans . .

(List continued on next page.)

OTHER PUBLICATIONS

. ", *Bulletin of World Health Org.*, vol. 62 (6), 1984, pp. 909–918.

Barrineau, P. et al., "The DNA Sequence Of The Mercury Resistance Operon of the IncFII Plasmid NR1", *J. Of Molecular and Applied Genetics*, vol. 2, No. 6, 1984, pp. 253–261.

Sporecke, I. et al., "Genetic Mapping Of *Vibrio cholerae* Enterotoxin Structural Genes", *J. Of Bacteriology*, vol. 157, No. 1, Jan. 1984, pp. 253–261.

Levine, M. et al., "Evaluation In Humans Of Attenuated *Vibrio cholerae* E1 Tor Ogawa Strain Texas Star–SR . . . ", *Infection and Immunity*, vol. 43, No. 2, Feb. 1984, pp. 515–522.

Kaper, J. et al., "Recombinant Nontoxinogenic *Vibrio cholerae* Strains As Attenuated Cholera Vaccine Candidates", *Nature*, vol. 308, Apr. 12, 1984, pp. 655–658.

Lockman, H. et al., "*Vibrio cholerae* Enterotoxin Genes: Nucleotide Sequence Analysis of DNA . . . ", *J. Of Bacteriology*, vol. 159, No. 3, Sep. 1984, pp. 1086–1089.

Kaper, J. et al., "A Recombinant Live Oral Cholera Vaccine", *Bio/Technology*, Apr. 1984, pp. 345–349.

Kaper, J. et al., "Development And Testing Of A Recombinan Live Oral Cholera Vaccine", *Vaccines 85, Cold Spring Harbor Lab.*, pp. 107–111.

Brown, N. et al., "The Nucleotide Sequence Of the Mercuric Resistance Operons Of Plamd R100 and Transposon TN501 . . . ", *Mol. Gen Genet*, 202, 1986, pp. 143–151.

Black, Robert. et al., "Protective Efficacy In Man Of Killed Whole Vibrio Oral Cholera Vaccine . . . ", Infection & Immun., 1987, 23 pages.

Kaper, J. et al., "Recent Advances In Developing A Safe And Effective Live Oral Attenuated *Vibrio cholerae* Vaccine", *Advan. In Research on Cholera & Related Diarrheas*, 6, eds. 1988, pp. 161–167.

Levine, M. et al., "Volunteer Studies Of Deletion Mutants Of *Vibrio cholerae* O1 Prepared By Recombinant Techniques", *Infection & Immunity*, vol. 56, No. 1., Jan. 1988, pp. 161–167.

Rader, A. et al., "Nucleotide Sequences And Comparison Of The Hemolysin Determinants . . . ", *Infection & Immunity*, vol. 56, No. 6, Jun. 1988, pp. 1414–1419.

Levine, M. et al., "Safety, Immunogenicity, And Efficacy Of Recombinant Live Oral Cholera . . . ", *The Lancet*, Aug. 28, 1988, pp. 467–470.

Migasena, S. et al., "Preliminary Assessment Of The Safety And Immunogenicity Of Live Oral Cholera . . . ", *Infection & Immunity*, vol. 57, No. 1, Nov. 1989, pp. 3261–3264.

Galen, J. et al., "Cloning, Sequencing, and Expression Of The Gene, nanH, For *Vibrio cholerae* . . . ", *Advances In Research On Cholera and Related Diarrheas*, 7, 1990, pp. 143–153.

Brickman, T. et al., "Molecular Cloning And Nucleotide Sequence Analysis Of Cholera Toxin Genes . . . ", *Infection & Immunity*, vol. 58, No. 12, Dec. 1990, pp. 4142–4144.

Cryz, S. Jr. et al., "Randomized Double-Blind Placebo Controlled Trial To Evaluate The Safety . . . ", *Vaccine*, vol. 8, Dec. 1990, pp. 577–580.

Fasano, A. et al., "*Vibrio Cholerae* Produces A Second Enterotoxin, Which Affects Intestinal Tight Junctions", *Proc. Natl. Acad. Sci. USA*, vol. 88, pp. 5242–5246, Jun. 1991.

Levin, M. et at., "Reactogenicity, Colonizing Capacity, and Immunogenicity of Further . . . ", *Abstracts 21st Joint Conference on Cholera*, Bethesda, Md., Oct. 21–23, 1985, pp. 37–38.

Kaper, J. et al., "Recent Advances in Developing A Safe and Effective Live Oral Attenuated *Vibrio cholerae* Vaccine", *Abst. 22nd Joint. Conf. US–Japan Cooperative Medical Sci. Prog.*, Toyama, Japan, *1986, p. 25.*

Kaper, J. et al., "A Safe And Effective Live Oral Attenuated *Vibrio cholerae* Vaccine", *Abstracts of the 1986 ICAAC*, (454) p. 180.

```
                A1
                XbaI
    ----  GAT  TCT AGA  CCT
          CTA  AGA TCT  GGA
          ASP  SER ARG  PRO

A2
                         ClaI
              TCA  TCG ATG  AGT
              AGT  AGC TAC  TCA   ----
              SER  SER MET  SER

A1           A2
              XbaI
    ----  GAT  TCT AGA  GCG ATG
          CTA  AGA TCT  CGC TAC   ----
          ASP  SER ARG  ALA MET
```

VIBRIO CHOLERAE STRAIN CVD103HG', METHOD OF MAKING SAME, AND VACCINES DERIVED THEREFROM

CROSS REFERENCE TO THE RELATED APPLICATIONS

This application is a continuation-in-part of applicants' U.S. patent application Ser. No. 07/757,930, filed Sep. 12, 1991, now abandoned, which is a continuation of Ser. No. 06/581,406, filed Feb. 17, 1984, issued as U.S. Pat. No. 5,135,862 on Aug. 4, 1992, which is a continuation-in-part of applicants' U.S. patent application Ser. No. 06/472,276, filed Mar. 4, 1983, abandoned, the entire specifications of which are incorporated herein by reference. The research outlined in this application was supported by the National Institute of Health.

BACKGROUND OF THE INVENTION

*Vibrio Cholerae* (*V.cholerae*) is a non-invasive enteropathogen of the small bowel that does not penetrate the mucosal surface. Local SIgA mediated immunity at the mucosal surface is therefore implicated as a protective mechanism. Pathogenic *V. cholerae* 01 elaborate a protein enterotoxin (also known as cholera enterotoxin, or choleragen, or cholera toxin) which is responsible for induction of copious secretion by the intestine resulting in watery diarrhea, the clinical consequence of cholera infection. Cholera diarrhea can be extraordinarily severe and result in loss of so much body water and salts that dehydration, acidosis, shock, and death ensue without prompt therapy.

The cholera vaccines that have been developed can be broadly divided into two categories; those aiming to stimulate antitoxic immunity and those intending to induce antibacterial immunity. Experiments with animal models support a protective role for either or both antitoxic and antibacterial immunity. It has been suggested that when both types of immunity work in unison, there is a synergistic effect. [Holmgren, J. et al. *J. Infect. Dis.* 136 Suppl., S105-S1122 (1977); Peterson, J. W. *Infect. Immun.* 26, 594 (1970); Resnick, I. G. et al. *Infect. Immun.* 13, 375 (1980); Svennerholm, A. -M. et al. *Infect. Immun.* 13, 735 (1976). However, it appears that protective immunity in humans can be conferred without such synergistic effect, that is by either antitoxic immunity or antibacterial immunity [Eubanks, E. R. et al. *Infect. Immun.* 15, 533 (1977); Fujita, K. et al. *J. Infect. Dis.* 125, 647 (1972); Holmgren, J., *J. Infect. Dis.*, supra; Lange, S. et al. *Acta Path. Microbiol. Scand Sect. C* 86, 145 (1978); Peterson, J. W., supra (1979); Pierce, N. F. et al. *Infect Immun.* 37, 687 (1982); Pierce, N. F. et al. *Infect. Immun.* 21, 185 (1978); Pierce, N. F. et al. *J. Infect. Dis.* 135, 888 (1977); Resnick, I. G. et al., supra; Svennerholm, A. -M. et al, supra].

KILLED WHOLE CELL VACCINES

1. Parenteral Whole Cell Vaccines

For almost a century, killed whole *V. cholerae* have been employed as parenteral vaccines; these vaccines are still commercially available. Experience with the parenteral whole cell vaccines has been reviewed recently in Joo, I., "Cholera Vaccines," in *Cholera*, (Barua D. and Burrows W., eds.), Saunders, Philadelphia, pp. 333-355 (1974) and in Feeley, J. D. et al., in *Cholera and Related Diarrheas*, 43rd Nobel Symp., Stockholm 1978, (O. Oucherlong, J. Holmgren, eds.) Karger, Basel, pp. 204-210 (1980). Such vaccines stimulate high titers of serum vibrioicidal antibodies. They also stimulate increases in intestinal SIgA antibody to *V. cholerae* somatic O antigen when given to Pakistanis but not to Swedes [Svennerholm, A. -M. et al. *Infect. Immun.* 30, 427 (1980); Svennerholm, A. -M. et al. *Scan. J. Immun.* 6, 1345 (1977)]. It has been suggested that the Pakistani vaccine recipients respond in this way because they are already immunologically primed from prior antigenic contact, while persons living in a non-endemic area (e.g., Sweden) are not. In field trials parenteral killed whole cell vaccines have been shown to confer significant protection against the homologous *V. cholerae* serotype, but usually for a period of less than one year [Joo, I. supra; Feeley, J. C. , supra; Svennerholm, A. -M. et al. supra, (1980); Svennerholm, A. -M. et al. supra, (1977); Mosley, W. H. et al. *Bull. Wld. Hlth. Org.* 49, 13 (1973); Phillipines Cholera Committee, *Bull. Wld. Hlth. Org.* 49, 381 (1973)]. There is some evidence to suggest that parenteral whole cell Inaba vaccine provides good, short term protection against Ogawa, as well as against Inaba cholera, while Ogawa vaccine is effective only against Ogawa.

By use of adjuvants, it has been possible to maintain a vaccine efficacy of approximately 70% for up to one-and-one-half years with parenteral vaccine (see, e.g., Saroso, J. S. et al. *Bull. Wld. Hlth. Org.* 56, 619 (1978)). However, the adverse reactions encountered at the site of inoculation with adjuvanted vaccines (which include sterile abscesses) are sufficiently frequent and severe to preclude routine use of such adjuvanted vaccines.

2. Oral Whole Cell Vaccines

Killed whole vibrios administered orally stimulate the appearance of local intestinal antivibrio antibody. [Freter, R. *J. Infect Dis.* 111, 37 (1972); Freter R. et al. *J. immunol.* 91 724 (1963); Ganguly, R. et al. *Bull. Wld. Hlth. Org.* 52, 323 (1975)]. Other investigators have shown substantial vaccine efficacy, but a large proportion of the vaccinees developed diarrhea after subsequent challenge with pathogenic vibrios [Cash, R. A. et al. *J. Infect. Dis.* 130, 325 (1974)].

TOXOIDS

Immunizing agents intended to prevent cholera by means of stimulating antitoxic immunity include:
1) Formaldehyde-treated cholera toxoid
2) Glutaraldehyde-treated cholera toxoid;
3) Purified B subunit; and
4) Procholeragenoid (with or without formaldehyde treatment).

1. Formaldehyde-Treated Cholera Toxoid

Treatment of purified cholera toxin in vitro with formaldehyde eradicates its toxicity, resulting in a toxoid that exhibits little toxic biological activity but stimulates antitoxic antibodies following parenteral immunization of animals. However, when the first toxoid of this type was administered to monkeys and man as a parenteral vaccine, the toxoid reverted to partial toxicity causing unacceptable local adverse reactions at the site of inoculation [Northrup, R. S. et al. *J. Infect. Dis.* 125, 471 (1972)]. An aluminum-adjuvanted formalinized cholera toxoid has been administered parenterally to Bangladeshi volunteers, including lactating mothers, but no field trials with this vaccine have been undertaken [Merson, M. H. et al. *Lancet* I, 931 (1980)]. Formalinized cholera toxoid prepared in the presence of glycine has also been tried by the parenteral route, but the vaccine showed no evidence of efficacy [Ohtomo, N. In *Proceedings of the 12th Joint Conference on Cholera*, U.S.-Japan Cooperative Medical Science Program, Sapporo (Fukumi H., Zinnaka Y., eds.) pp. 286–296 (1976); Noriki, H. In *Proceedings of the 12th Joint Conference on Cholera*, U.S.-Japan Cooperative Medical Science Program, Sapporo (Fukumi H., Zinnaka Y., eds.) pp. 302–310 (1976)].

2. Glutaraldehyde-Treated Cholera Toxoid

Methods have been developed for the large-scale preparation of a glutaraldehyde-treated cholera toxoid that is essentially free of contaminating somatic antigen [Rappaport, E. S. et al. *Infect. Immun.* 14, 687 (1976)]. It was hoped that this antigen could be used to assess in a "pure" manner the protective role of antitoxic immunity alone. A large-scale field trial of this toxoid given as a parenteral vaccine was carried out in Bangladesh in 1974 [Curlin, G. et al. In *Proceeding of the 11th Joint Conference on Cholera*, U.S.-Japan Cooperative Medical Science Program. pp. 314–329, New Orleans, (1975)]. The toxoid stimulated high titers of circulating antitoxins in Bangladeshi recipients. Two waves of cholera, El Tor Inaba followed by El Tor Ogawa, struck the field area allowing a fair evaluation of vaccine efficacy. A protective effect could be demonstrated in only one age group and was restricted to the period of the Inaba epidemic, so that glutaraldehyde-treated cholera toxoid given alone as a parenteral vaccine provided little protection and was substantially inferior to similar field trials in the same population with parenteral killed whole cell vaccines.

The use of glutaraldehyde-treated cholera toxoid as an oral vaccine has been investigated on the assumption that toxoid given by this route might be more efficient by stimulating intestinal antitoxin [Levine, M. M. et al. *Trans. Roy. Soc. Trop. Med. Hyg.* 73, 3, (1979)]. Two groups of volunteers were immunized with three 2.0 mg., or three 8.0 mg doses of toxoid given directly into the small intestinal lumen (via intestinal tube) at monthly intervals. The vaccinees and unimmunized controls then participated in experimental cholera challenge studies. In neither challenge study was the attack rate or severity of diarrhea significantly diminished in the vaccinees when compared with controls. The lack of efficacy of oral glutaraldehyde-treated cholera toxoid may be due to the fact that the capacity of B subunits to bind to GM1 ganglioside is greatly diminished as a consequence of toxoiding with glutaraldehyde.

3. Purified B Subunit

Cholera enterotoxin is composed of two subunits designated A and B. The A subunit induces the enzymatic changes which lead to fluid secretion, while the non-toxic B subunit is the immunogenic moiety that binds to the receptor for toxin (GM1 ganglioside) on intestinal epithelial cells [Holmgren, J. *Nature* 292, 413 (1981)]. It has been shown that purified B subunit given either orally or parenterally to Bangladeshis stimulates the appearance of SIgA antitoxin in intestinal fluid, a result attributable to immunological priming in a cholera-endemic area [Svennerholm, A. -M. et al. *Lancet I*, 305 (1982)].

The major advantages of B subunit oral vaccine to stimulate antitoxic immunity include its complete safety (there is not potential for reversion to toxin as exists with toxoids) and retention of its capacity to adhere to toxin receptors on enterocytes. Animal studies suggest that it is less potent than native holotoxin in stimulating antitoxin [Pierce, N. F. supra, (1982)].

It will be understood that the purified B subunit can be used, if at all, in conjunction with e.g. oral killed vibrios as a combination oral vaccine intended to stimulate both antibacterial and antitoxic antibodies.

4. Procholeragenoid

Procholeragenoid is the large molecular weight toxoid (ca. 1,000,000 MW) that results when cholera enterotoxin is heated at 65° C. for at least five minutes [Finkelstein, R. A. et al. *J. Immunol.* 107, 1043 (1971)]. It is immunogenic while retaining less that 5% of the biological toxic activity of the parent toxin. Heating for longer times (e.g., 25 minutes) produces less biological toxicity [Germanier, R. et al. *Infect. Immul* 13, 1692 (1976)], and subsequent treatment with formaldehyde completely abolishes residual biological toxicity. The resultant formaldehyde-treated procholeragenoid is at least as potent as the parent toxin in stimulating serum antitoxin following immunization of rabbits. Swiss volunteers developed brisk serum antitoxin responses following parenteral immunization with 10, 30, or 100 mcg doses of formaldehyde-treated procholeragenoid [Germanier, R. et al. *J. Infect. Dis.* 135. 512 (1977)]. No notable adverse reactions were observed.

As an oral antigen procholeragenoid is more immunogenic when given in the form without formaldehyde-treatment. In dogs, untreated procholeragenoid is tolerated well as an oral vaccine; oral doses (with $NaHCO_3$) up to 500 mcg do not cause diarrhea. Five 500 mcg doses spaced over 42 days stimulate significant protection in dogs against oral challenge with pathogenic *V. cholerae*. Doses of 50 mcg and 200 mcg with $NaHCO_3$ have been given to groups of six and four adult volunteers, respectively, without eliciting adverse reactions.

It will be understood that procholeragenoid can be used in conjunction with e.g. killed vibrios or other relevant antigens capable of stimulating antibacterial immunity so that the antitoxic immunity induced by procholeragenoid is enhanced.

COMBINATION VACCINES

The major attraction of non-living, oral cholera vaccine is its safety. An oral vaccine consisting of a combination of antigens, intending to stimulate both antibacterial and antitoxic immunity, would be most likely to succeed for the following reasons: Toxoid vaccines that stimulate purely antitoxic immunity have not been shown to be efficacious in protecting man against cholera, although they may protect animal models. In addition, oral or parenteral killed whole cell vaccines that stimulate no antitoxic immunity provide significant protection against cholera in man, albeit for a short period of time. Furthermore, combinations of antigens (such as crude cholera toxin, or toxin plus lipopolysaccaride) that stimulate both antitoxic and antibacterial immunity, give synergistic protection.

Two studies so far have been carried out in many with combination vaccines. In the first, nine volunteers who ingested glutaraldehyde-treated cholera toxoid (2 mg weekly for four weeks) plus killed El Tor Inaba vibrios ($10^{10}$ vibrios twice weekly for four weeks) were challenged after one month with $10^6$ pathogenic El Tor Inaba vibrios, along with six unimmunized controls. Diarrhea occurred in only two of nine vaccinees, versus four of six controls (vaccine efficacy 67%) and illness was clearly attenuated in the two ill vaccinees. More pertinent, perhaps, is the observation that *V. cholerae* could be directly cultured from stools of only two of nine vaccinees, versus six of six controls. This demonstrates that immunologic mechanisms impeded the proliferation of vibrios.

More recently, three doses of B subunit/killed whole cell vaccine was given to adult volunteers who participated in a vaccine efficacy challenge. The combination vaccine was give on days 0, 14, and 28. Each of the three doses of vaccine contained 0.5 mg of purified B subunit and $2 \times 10^{11}$ killed *V. cholerae* ($5 \times 10^{10}$ classical Inaba, $5 \times 10^{10}$ classical Ogawa, and $1 \times 10^{11}$ El Tor Inaba).

A group of eleven volunteers immunized with this combination vaccine were challenged one month after their last dose with $10^6$ pathogenic *V. cholerae* El Tor Inaba, along with seven control volunteers. Diarrhea occurred in seven of seven controls, but in only four of eleven vaccinees (p=0.01). The illness in the four vaccinees was definitely milder.

Thus, results of studies with oral toxoid/killed whole cell vaccine combinations demonstrate a measurable degree of efficacy. The protective vaccine efficacy, however, is only moderate (55-65%) and multiple doses are required to induce the protection.

ATTENUATED V. CHOLERAE VACCINES

Both classical and El Tor clinical cholera infections stimulate a high degree of protective immunity for at least three years in North American volunteers [Cash, R. A. et al., supra (1974); Levine, M. M. et al., supra (1979); Levine, M. M. et al. "Volunteers studies in development of vaccines against cholera and enterotoxigenic *Escherichia coli*: a review," in *Acute Enteric Infections in Children: New Prospects for Treatment and Prevention.* (T. Holm, J. Holmgren, M. Merson, and R. Mollby, eds.) Elsevier, Amsterdam, pp. 443-459 (1981); and Levine, M. M. et al. *J. Infect. Dis.* 143, 818 (1981)]. Based on these observations in volunteers, perhaps the most promising approach toward immunologic control of cholera may be with attenuated non-toxigenic *V. cholerae* strains employed as oral vaccines.

1. Naturally-Occurring Strains

Non-toxigenic *V. cholerae* 01 strains isolated from environmental sources in India and Brazil have been evaluated in volunteers as potential vaccine candidates with disappointing results. They either failed to colonize the intestine of man, or did so minimally; vibrocidal antibody responses were meager, and they failed to provide protection in experimental challenge studies [Cash, R. A. et al. *Infect. Immun.* 10, 762 (1974); Levine M. M. et al. *J. Infect. Dis.* 145, 296 (1982)]. Many of these strains appear to lack the toxin gene, as measured by hybridization with a radioactive DNA probe [Kaper, J. B. et al. *Infect. Immun.* 32, 661 (1981)].

2. Mutagenized Attenuated Strains

Classical Inaba 569B has been mutagenized with nitro-soguanide (NTG) and a hypotoxinogenic mutant isolated [Finkelstien, R. A. et al. *J. Infect. Dis.* 129, 117 (1974); Holmes, R. K. et al. *J. Clin. Invest.* 55, 551 (1975). This mutant strain, M13, was fed to volunteers. Diarrhea did not occur but the strain colonized poorly. Challenge studies demonstrated that some protective efficacy was conferred by immunization with multiple doses [Woodward, E. et al. *Develop. Biol. Stand.* 33., 108, (1976)].

El Tor Ogawa 3083 has also been mutagenized [Honda, T. et al. *Proc. Nat. Acad. Sci.* 76, 2052 (1979)]. Brute force selection and analysis of thousands of colonies yielded one isolate that continued to produce the immunogenic B subunit while failing to produce detectable A subunit or holotoxin. The one isolate, Texas Star-SR, fulfilled these criteria. Texas Star-SR produces normal or increased amount of B subunit but is negative in assays for holotoxin activity or A subunit activity.

Texas Star-SR has been extensively evaluated in volunteers (see, e.g., Levine M. M. et al. *Acute Enteric,* supra. (1981)). Groups of five volunteers received two $10^9$ organism doses one week apart and eighteen more volunteers ingested two $2 \times 10^{10}$ organism doses one week apart. Some degree of diarrhea was seen in sixteen of the sixty-eight vaccinees (24%). In only one individual did the total stool volume exceed 1.0 liter (1464 ml). Typically, the vaccine-induced diarrhea consisted of two or three small, loose stools totalling less than 400 ml in volume. Vaccine organisms were recovered from coprocultures of approximately one-half of the vaccine recipients. Where jejunal fluid was cultured (recipients of doses of $10^8$ or more vaccine organisms), cultures were positive in thirty-five of forty-six vaccinees (76%). Hundreds of Texas Star clones recovered from coprocultures and jejunal fluid cultures were examined for cholera holotoxin by the sensitive Y-1 adrenal cell assay; none were positive.

Significant rises in serum antitoxin were detected in only 29% of the vaccinees; however, 93% manifested significant rises in serum vibriocidal antibody and the titers were substantially close to those encountered following infection with pathogenic *V. cholerae*. In experimental challenge studies in volunteers, Texas Star-SR was found to confer significant protection against challenge with both EL Tor Ogawa And El Tor Inaba vibrios. One or two doses of Texas Star-SR attenuated oral vaccine confers good protection against El Tor cholera.

It is clear that the use of attenuated strains has intrinsic advantages since such strains mimic infection-derived immunity to cholera. However, the Texas Star-SR strains suffers from certain drawbacks. To begin with, mutagenesis (e.g., with nitrosoguanidine) induces multiple mutations, not all of which are necessarily recognized. Furthermore, the precise genetic lesion that is presumed to be responsible for the attenuation of Texas Star-SR is not known. In addition, Texas Star-SR may revert to virulence, like any pathogen mutated with nitrosoguanidine.

Applicants of the present invention have isolated, by a novel method, deletion mutants of a virulent strain of *Vibrio cholerae* known to produce both immunity and disease in volunteers. The deletions are restriction endonuclease fragments. The vaccine strains of the present invention have been specifically altered through the use of recombinant DNA techniques to render the avirulent without affecting other components necessary for immunity. This attenuation was accomplished by using restriction endonucleases which cleave the DNA of the bacterium at specific sites, to specifically delete the genes responsible for cholera toxin (i.e., the ctx gene). Plasmids carrying the ctx gene were digested with restriction endonucleases to delete the ctx gene, but were constructed to retain extensive lengths of flanking DNA of the *V. cholerae* chromosome. Conjugal gene transfer of the plasmids into *V. cholerae* yielded an avirulent *V. cholerae* strain carrying the extrachromosomal copies of the plasmids. Subsequent conjugation with cells having other plasmids produced, after appropriate selection of selectable plasmid markers, *V. cholerae* strains having deletions in the ctx regions. Such nontoxigenic deletion mutants would then be capable of colonizing the small intestine and stimulating local, protective immunity directed against the bacterial cell. After the transient colonization episode, the vaccine would be protective against subsequent disease symptoms which would normally occur upon challenge with virulent toxigenic *V. cholerae* strains.

The genes for *V. cholerae* toxin have been cloned [Pearson, G. D. N. et al. *Prod. Nat. Acad. Sci.* 79, 2976 (1982); Kaper, J. B. et al. *Amer. Soc. Micribiol. Abstr. Annu. Meeting, Atlanta, Georgia*, 36 (1982); Kaper, J. B. et al. *Symposium on Enteric Infections in Man and in Animals: Standardization of Immunological Procedures*, Dublin, Ireland, Abstract No. 2.5 (1982)]. Toxin structural gene deletion mutants of *V. cholerae* have been isolated, but only by infection with mutagenic vibriophages capable of integration at random sites along to chromosome [Mekalanos, J. J. et al. *Proc. Nat. Acad. Sci.* 79, 151, (1982)]. Recombination in *Vibrio cholerae* has been reported, but it has not been used to isolate restriction fragment deletions in the ctx genes for vaccination purposes [Parker, C. et al. *J. Bact.* 112, 707 (1972); Johnson, S. R. et al. *Molec. Gen. Genet.* 170, 93 (1979); Sublett, R. D. et al. *Infect. Immun.* 32 1132 (1981) and Thomson, J. A. et al. *J. Bact.* 148, 374 (1981)].

BRIEF DESCRIPTION OF THE INVENTION

A culture of *Vibrio cholerae* is described comprising a *Vibrio cholerae* strain having a restriction endonuclease fragment of DNA deleted to confer avirulence and to retain capacity to colonize the intestine of a host animal. One isolated deletion mutant encompasses a deletion in the tox gene, as defined by Acc I restriction endonuclease sites.

A method of isolating such deletion mutants of *Vibrio cholerae* is also described, comprising the steps of
(a) constructing a first plasmid comprising *Vibrio cholerae* flanking sequences of one or more deleted restriction endonuclease fragments and a gene for a first selectable marker of foreign origin ligated to said flanking sequences to substitute for and to be in the place of said deleted fragment, wherein said sequences are of sufficient length to promote detectable in vivo recombination;
(b) mating a virulent strain of *Vibrio cholerae* with a first microorganism carrying the first plasmid;
(c) selecting for *Vibrio cholerae* expressing the first selectable marker;
(d) mating the selected product of step (c) with a second microorganism carrying a second plasmid with a second selectable marker, said second plasmid being incompatible with the first plasmid; and
(e) selecting for *Vibrio cholerae* expressing both the first selectable marker and the second selectable marker.

The *Vibrio cholerae* deletion mutants of this invention are useful in vaccination against cholera.

One *Vibrio cholerae* strain of the present invention, designated CVD103Hg$^r$, confers substantially close to 100% efficacy in humans against subsequent disease symptoms after challenge with a strain of a similar serotype.

Abbreviations for restriction endonuclease sites in the drawings are as follows:

A = Acc I restriction endonuclease site
B = Bgl II restriction endonuclease site
C = Cla I restriction endonuclease site
E = Eco RI restriction endonuclease site
H = Hind III restriction endonuclease site
P = Pst I restriction endonuclease site
S = Sal I restriction endonuclease site
X = Xba I restriction endonuclease site Other abbreviations in the drawings and elsewhere include:

Ap = Ampicillin resistance gene
Ap$^r$ = Ampicillin resistance phenotype
Ap$^s$ = Ampicillin sensitive phenotype
Chrom = Chromosome
Cm = Chloramphenicol resistance gene
CT = Cholera toxin
CTA = gene for A subunit of cholera toxin
CTB = gene for B subunit of cholera toxin
kb = Kilobases
p = plasmid
Su = Sulfonamide
Su$^r$ = Sulfonamide resistance phenotype
Tc = tetracycline
Tc$^s$ = tetracycline sensitive phenotype
Tp = Trimethoprin

DETAILED DESCRIPTION OF THE INVENTION

The principle of the present invention is the isolation of a *Vibrio cholerae* vaccine strain specifically altered through recombinant DNA technology to render it avirulent without affecting other components necessary for immunity. This attenuation was accomplished by restriction endonuclease digestion of plasmids carrying appropriate *V. cholera* sequences, to specifically delete the genes coding for cholera toxin, or portion thereof. Conjugal gene transfer of these digested plasmids, followed by procedures for selecting in vivo recombinants with virulent host *V. cholera*, resulted in strains without the toxin genes or portion thereof. It will be understood that the methods of the present invention are applicable to the isolation of other deletion mutants of virulent *V. cholerae*, or to the isolation of strains having all or part of such deleted sequences reintroduced into the *V. cholerae* cell.

The starting material for the vaccine was the toxigenic *Vibrio cholerae* strain N16961, which has been demonstrated to produce in volunteers both typical diarrheal disease and strong, protective immunity to subsequent infection [Levine, M. M. et al., *Acute enteric*, supra. 1981]. The region of the bacterial chromosome which was found to be responsible for production of cholera toxin was cloned into the plasmid cloning vehicle pBR325, after screening Hind III digest of *V. cholerae* with an *E. coli* heat-labile enterotoxin gene probe [Kaper et al. *Amer. Soc.*, supra; Kaper et al. *Symposium*, supra]. The *V. cholerae* chromosome fragment was found to contain all genes necessary for toxin production. Next, this chromosomal region was then analyzed and mapped for the exact portions containing the toxin genes [Kaper, J. B. et al. *Lancet II,* 1162 (1981)]. Restriction enzymes were employed to cut out the DNA fragments containing these genes and a DNA fragment encoding a selectable marker (e.g., resistance to ampicillin) was inserted by ligation. The ampicillin resistance gene and the flanking Vibrio DNA were then cloned in a derivative of pRK290 which can be transferred from *E. coli* to *V. cholerae*. The resulting plasmid, pJBK55, was transferred from *E. coli* K-12 to *V. cholerae* N16961 by conjugation.

Figure 1:
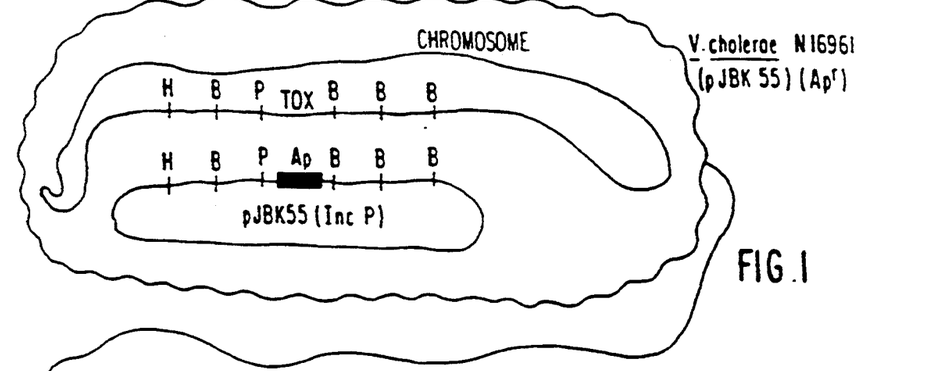
FIG. 1. *V. cholerae* N16961 (pJBK55) (Ap$^r$)
FIG. 2. Processes of crossing-over and conjugal gene transfer to construct *V. cholerae* JBK56.
Figure 2:
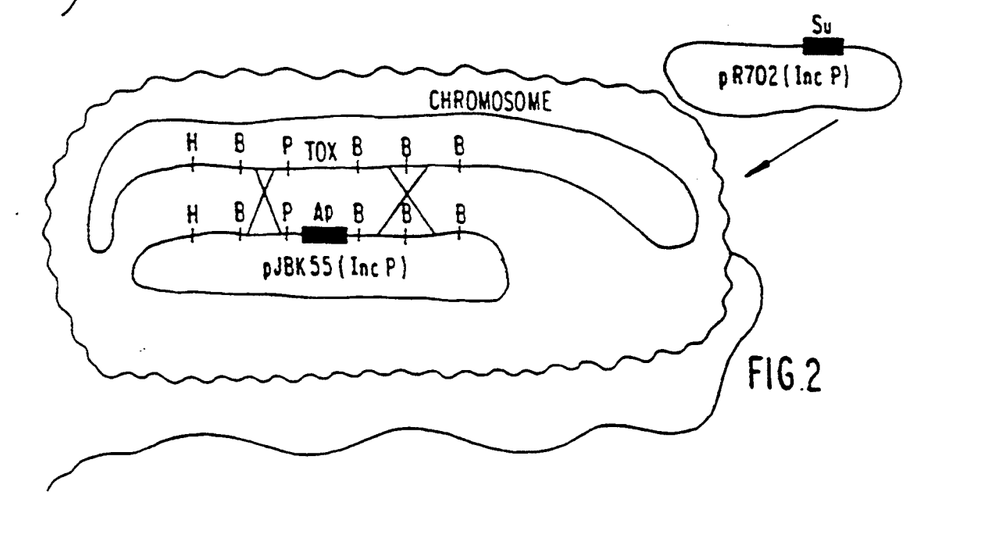
Figure 3:
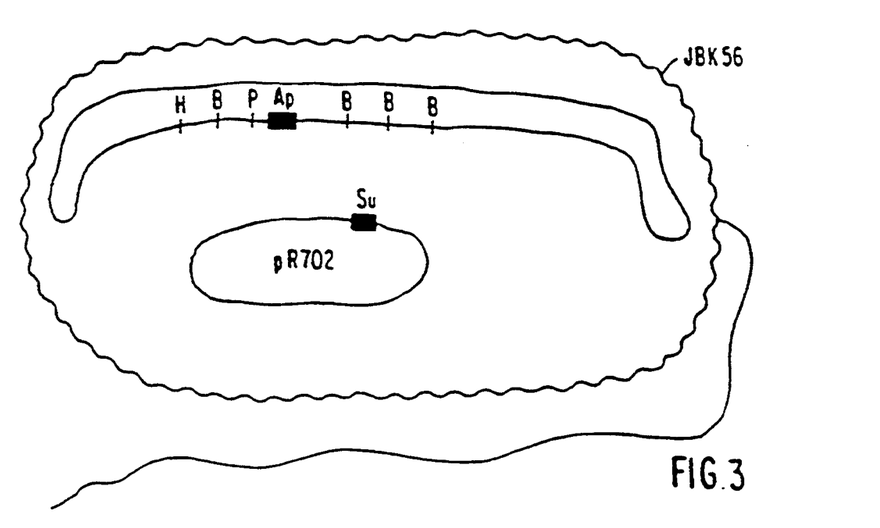
FIG. 3. *V. cholerae* JBK56.

The resulting strain, *V. cholerae* N16961 (pJBK55) (Ap$^r$) contained a region in its chromosome having intact toxin genes and, in an extrachromosomal state, a plasmid containing this same region with the toxin genes deleted and a gene for ampicillin substituted. (See FIG. 1.) At a low frequency, perhaps one in $10^6$ to one in $10^8$, the identical regions flanking the chromosomal toxin genes and the extrachromosomal (plasmid) ampicillin resistance gene will exchange and "cross over" or undergo in vivo recombination so that the region of DNA containing the resistance gene displaces the toxin gene on the chromosome (FIG. 2). This rare event is selected by testing a mixture of mutated and non-mutated cells for individual cells which are able to serve as host for an incoming incompatible plasmid [Ruvkun, G. B. et al. *Nature* 289, 85 (1981)]. Plasmids are divided into groups designated A through W, the members of which cannot stably coexist with each other. For example, a plasmid of incompatibility group P cannot be stably maintained in the same cell as another P group (Inc P) plasmid. Thus, Inc P plasmids, such as R702, which confers resistance to sulfonamide, cannot be maintained in a cell which has another Inc P plasmid such as PRK 290, pJBK45, or pJBK55. Therefore, R702 can be maintained in a strain in which the ampicillin resistance has recombined into the chromosome but not one in which an Inc P plasmid (e.g. pJBK55) is replicating extrachromosomally. By mating an *E. coli* strain containing Inc P R702 (sulfonamide resistance) and *V. cholerae* pJBK55 (ampicillin resistance) and selecting for *V. cholerae* which are resistant to both ampicillin and sulfonamide, colonies are isolated in which the sulfonamide resistance is mediated extrachromosomally by p702 and the ampicillin resistance is mediated chromosomally through substitution of the ampicillin resistance gene for the toxin gene (FIG. 3). One such strain, designated *V. cholerae* JBK56 was isolated and when tested for toxin production was found to be nontoxinogenic.

The final version of the vaccine strain, JBK70, was produced by substituting resistance to ampicillin, a therapeutically useful antibiotic, with resistance to mercury. This substitution was accomplished by cloning a gene for mercury resistance directly into the ampicillin resistant gene of pJBK55, thereby inactivating ampicillin resistance and conferring mercury resistance. The resulting plasmid, pJBK66 was also incompatible with R702 and was transferred to *V. cholerae* JBK56. A mutant in which the mercury resistance was recombined into the chromosome was selected using the Inc P plasmid R702 and selecting for *V. cholerae* which were ampicillin sensitive, mercury resistant, and sulfonamide resistant. A spontaneous derivative was later selected which was cured of pR702. The final mutant, JBK70, was nontoxinogenic and resistant to mercury only.

The vaccine strain *V. cholerae* JBK70 is one of the Inaba serotype. The other major serotype of *V. cholerae* is the Ogawa serotype. It is expected that a vaccine prepared from one serotype will protect against the other serotype. In the event that this is not the case, a live vaccine strain can be prepared from an Ogawa serotype and confer protection in volunteers [Levine, M. M. et al. *Acute enteric*, supra (1981)]. The exact mutation created in strain *V. cholerae* Inaba JBK56 was recreated in strain E7946 by directly transferring the region of the chromosome containing the ampicillin resistance in place of the toxin gene in JBK56 into E7946 through genetic recombination mediated by P, the sex factor of *V. cholerae* [Parker, C. et al., supra]. The P factor, which is distinct from Inc P plasmid, was transferred into JBK56 and was then mated with a rifampin resistant mutant of E7946. By selection of a mutant which was resistant to both ampicillin and rifampin, a vaccine strain was isolated which was of the Ogawa serotype with the toxin genes completely deleted.

If antibacterial immunity is insufficient for protection, then an antitoxic component can be added by adding back the genes for production of cholera toxin B but not A subunit. This has been accomplished by cloning the B subunit gene into the cloning vector pMS9. The resulting plasmid, pJBK51, produces high levels of B subunit and was reintroduced into the nontoxic vaccine strain *V. cholerae* JBK70 to make an attenuated vaccine strain JBK70 (pJBK51) which fails to produce the A subunit.

The vaccine strains of the present invention are derived inter alia from *V. cholerae* N16961 having the serotype Inaba. It will be understood that other strains or other biotypes and serotypes can be used to substitute for N16961 to produce vaccine strains having specific deletions in the tox gene or genes, or in other locations along the *V. cholerae* chromosome. Since the object of isolating such vaccine strains is to mimic the infection process without the associated pathological phenomena, site-directed mutagenesis of virulent strains, as described in this application, produces substantial possibilities in the prophylactic vaccination against cholera.

For example, applicants have produced another *V. cholerae* vaccine strain CVD101, characterized by a deletion of most of the A subunit gene present in 2 copies of the tox gene. It is expected that the efficacy of CVD101 is substantially close to 100%, since the parent strain 395 confers 100% efficacy.

Construction of CVD101 followed in general the principles outlined supra, e.g. the construction of JBK70, except that the resulting CVD101 had no resistance gene that needed curing. The final step in isolating an in vivo recombinant included a scheme for selecting sensitivity to an antibiotic e.g. tetracycline sensitivity, whereas the parent strain had inserted at the location of the A gene of CT a tetracycline resistance gene. It will be understood that such antibiotic sensitivity is another example of a selectable marker.

Applicants have produced another *V. cholerae* vaccine strain CVD103, which is a derivative of *V. cholerae* strain 569B. The same mutation was made in 569B to derive CVD103 as was made in CVD101, which is described above. The procedure used to prepare CVD103 is the same procedure used to prepare CVD101, except that 569B was used rather than 395. CVD103 is a derivative of wild-type strain classical Inaba 569B that has a fragment of DNA coding for the $A_1$ subunit of cholera toxin deleted.

Applicants have produced another *V. cholerae* vaccine strain, CVD103Hg$^r$, which is a derivative of CVD103. CVD103Hg$^r$ has a mercury resistance gene incorporated in the chromosome of CVD103.

Production of vaccine strains can be performed by a variety of methods, including the following: *Vibrio cholerae* is subcultured from stock cultures into brain/heart infusion agar (BHIA) and grown at 37° C. overnight. Identity is tested with group- and type-specific antisera and twenty to thirty colonies are suspended in BHI broth. Preincubated BHIA plates are inoculated with BHI suspension. After incubation for five to six hours, each plate is harvested with 5 ml of sterile saline buffered to pH 7.2±0.1. Harvested organisms are centrifuged in the cold at 750 g for ten minutes, resuspended and washed twice in four-times the original volume. The suspension is standardized spectrophotometrically and diluted to approximately the number of organisms required for vaccination (ca $10^6$, which varies depending on the results of volunteer studies). Replicate, pourplate quantitative cultures are made of the inocula before and after challenge to confirm inoculum size. The final inoculum is examined with Gram's stain and agglutinated with homologous antiserum prior to feeding.

The *Vibrio cholerae* strains of the present invention can be administered by the oral route. Two grams of NaHCO$_3$ are dissolved in five ounces of distilled water. Volunteers drink four ounces of the NaHCO$_3$/water; one minute later the volunteers ingest the vibrios suspended in the remaining one ounce of NaHCO$_3$/water. Volunteers are NPO ninety minutes pre- and postinoculation.

With regard to safety, the major concern is that the vaccine strain does not revert to toxigenicity (i.e., produce intact cholera toxin) which could cause disease. The two major assays for testing toxin are the Y-1 adrenal cell assay [Sack, D. A. et al. *Infect. Immjun.* 11, 334 (1975)] and the enzyme-linked immunosorbent assay (ELISA) [Sack, D. A. et al. *J. Clin. Micro.* 11, 35 (1980)]. The vaccine strain (JBK70) has been repeatedly tested in these two assays and found to be negative each time. Far more important, however, are the genetic assays performed for the presence of toxin genes. The DNA for cholera toxin genes can be radioactively labeled and used as a specific probe to identify other cholera toxin genes in the strain, according to the method of Southern, E. M. *J. Mol. Bio.* 98, 503 (1975). When tested by this method, the vaccine strain described in the invention possesses no detectable genetic material that can encode cholera toxin. The vaccine has also been tested in an infant mouse model, according to Baselski, V. et al. *Infect. Immun.* 15, 704 (1977). After repeated (ten in all) serial passages, no fluid accumulation (i.e., evidence of disease, has been found. As expected, JBK70 was found to colonize the infant mouse intestine.

In the examples that follow, any of the techniques, reactions, and separation procedures are already well known in the art. All enzymes, unless otherwise stated, are available from one or more commercial sources, such as New England BioLabs—Beverly, Mass.; Collaborative Research—Waltham, Mass.; Miles Laboratories—Elkhart, Ind.; Boehringer Biochemicals Inc.—Indianapolis, Ind.; and Bethesda Research Laboratory—Rockville, Md., to mention a representative few. Buffers and reaction conditions for restriction enzyme digestion are used according to recommendations supplied by the manufacturer for each enzyme, unless indicated otherwise. Partial digestions with restriction enzymes are carried out using a reduced enzyme concentration which must be predetermined from preliminary experiments for each enzyme batch. Standard methodology for other enzyme reactions, gel electrophoresis separations, and *E. coli* transformation may be found in *Methods in Enzymology* Volume 68, Ray Wu, editor, Academic Press (1979). Another standard reference is Maniatis, T. et al. *Molecular Cloning*, Cold Spring Harbor (1982). Bacteria were grown according to procedures generally described in Miller, *Experiments in Molecular Genetics*, Cold Spring Harbor Laboratory (1972) *Vibrio cholerae* were propagated according to procedures generally described in Lennett, E. A. et al., eds., *Manual of Clinical Microbiology* 3rd Edition, American Society of Microbioloy, Washington (1980). *E. coli* and *V. cholerae* were mated according to procedures generally described in Johnson, Steven R. et al. *J. Bact.* 137, 531 (1979); and Yokata, T. et al. *J. Bact.* 109, 440 (1972).

The strains of this invention have been deposited at the American Type Culture Collection, located in Rockville, Md., prior to execution of the present application. The strains deposited are *V. cholerae* JBK56, *V. cholerae* JBK70, *V. cholerae* N16961, *V. cholerae* JBK70 (pJBK51), *V. cholerae* Ogawa 395, CVD101, CVD103Hg$^r$ which have ATCC accession numbers 39,317, 39,318, 39,315, 39,316, 39,541, 39,540 and 55,456 respectively.

EXAMPLE 1

Figure 4:
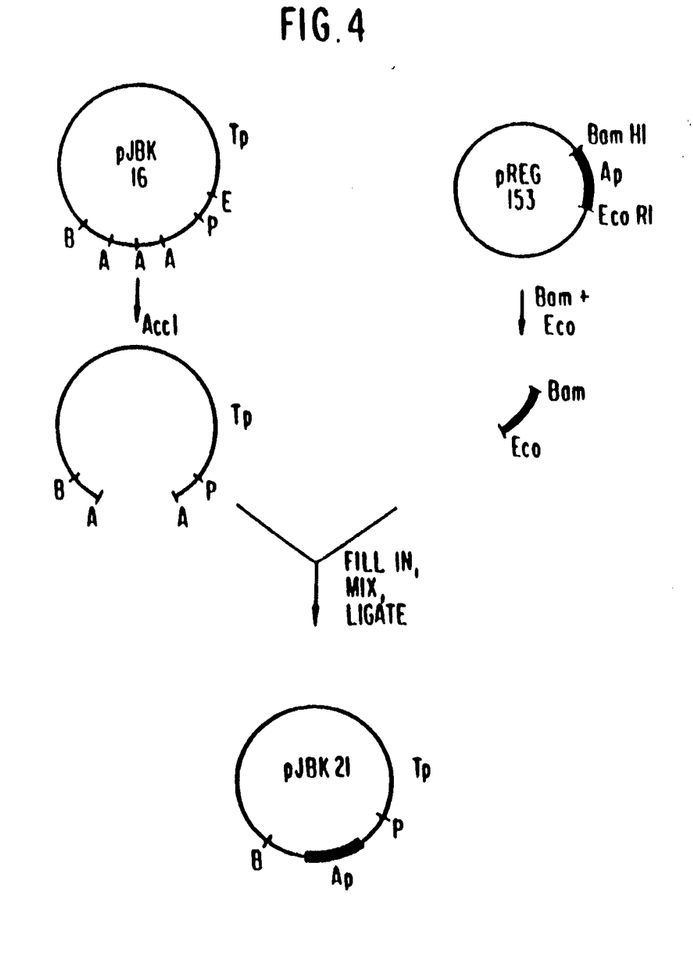
FIG. 4. Scheme for construction of JBK21.
Figure 5:
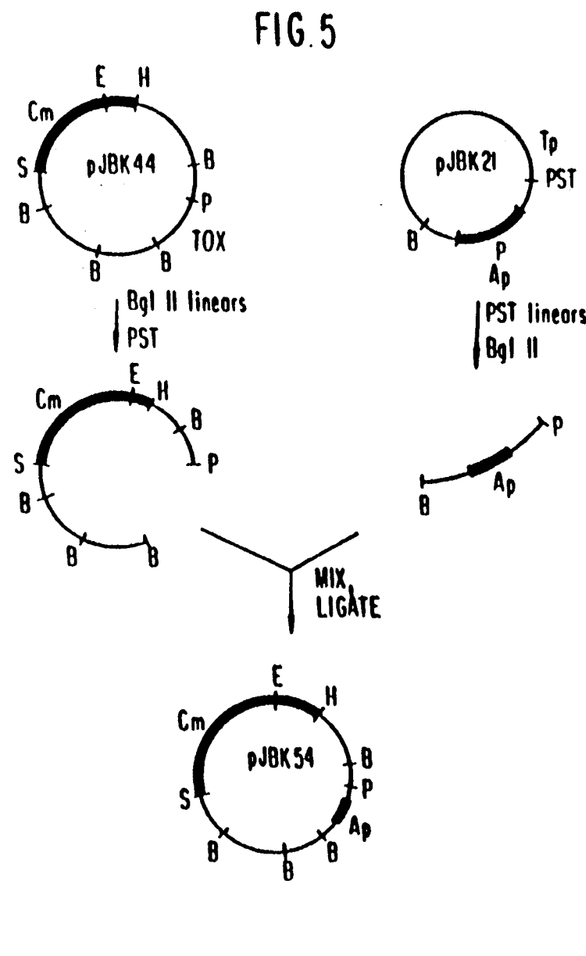
FIG. 5. Scheme for construction of pJBK54.
Figure 6:
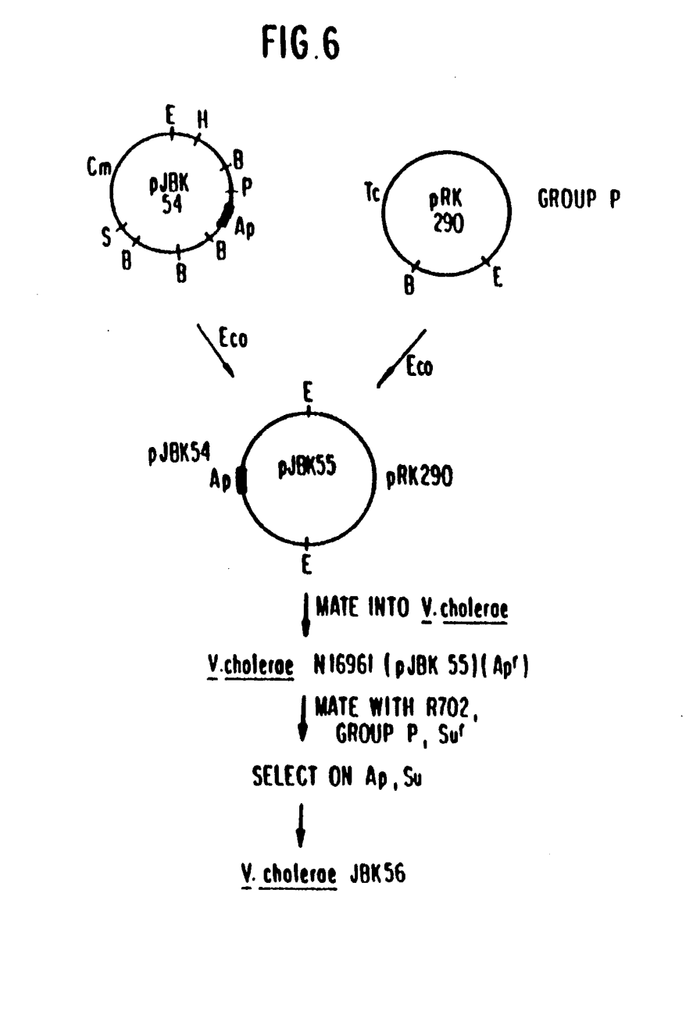
FIG. 6. Scheme for construction of *V. cholerae* JBK56.
Figure 7:
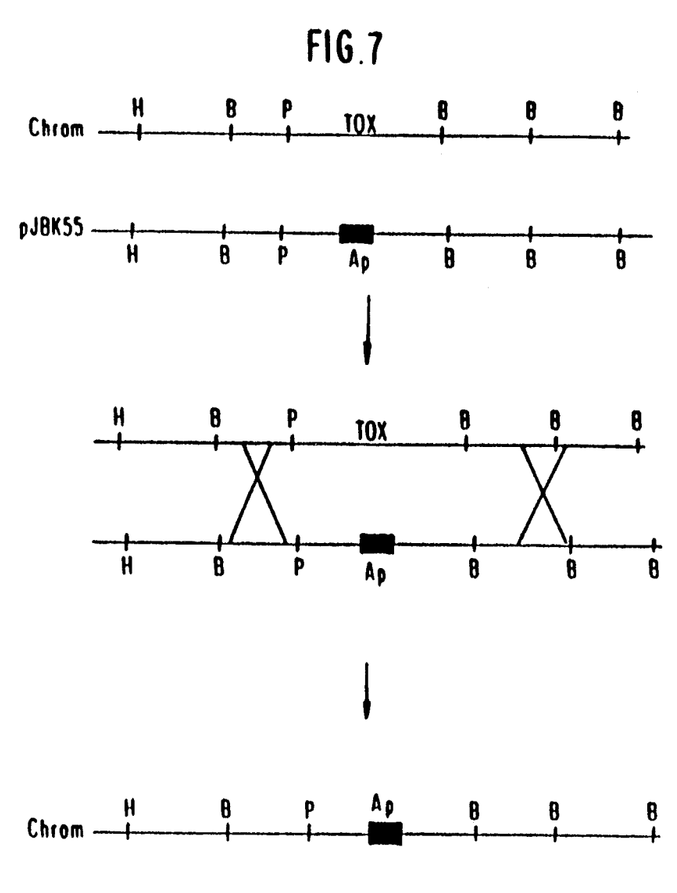
FIG. 7. Recombination in vivo by cross over and elimination of tox gene.
Figure 8:
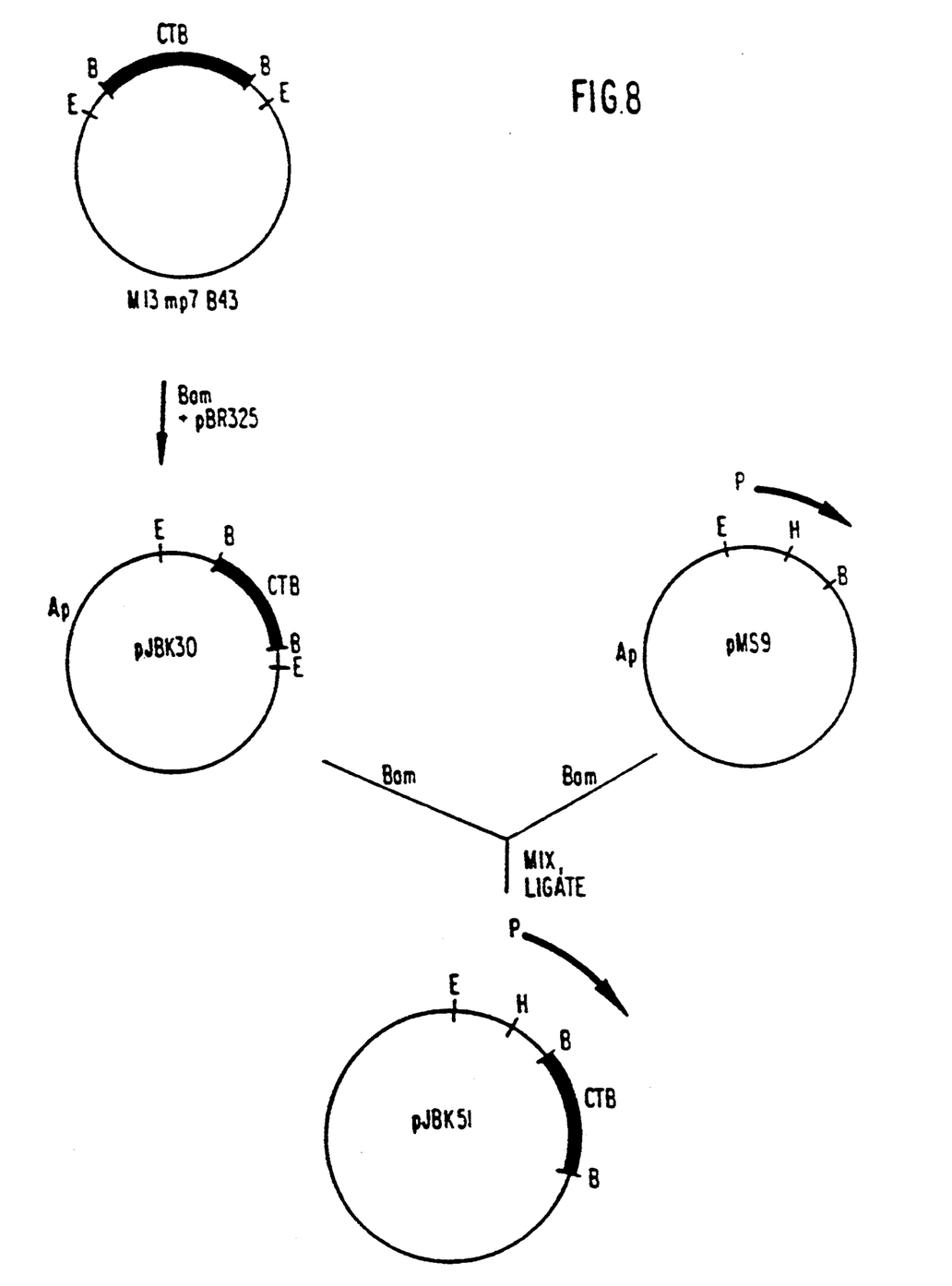
FIG. 8. Scheme for construction of pJBK51.

Construction of a Plasmid Having a Selectable Marker Gene Inserted to Replace to Toxin Genes The plasmid JBK16 contains a 4 kb PstI-BglII fragment of the chromosome containing the toxin genes. The toxin genes are flanked by Acc I sites and contain an internal Acc I site. JBK16 was digested to completion with Acc I and the Acc I fragments containing the toxin genes were separated from the rest of the plasmid. The remaining overlapping or "sticky" Acc I ends were made blunt-ended by "filling in" with the Klenow fragment of *E. coli* polymerase (i.e., the single-stranded DNA remaining after Acc I digestion were made double-stranded with flush ends). A gene encoding ampicillin resistance was purified from the plasmid pREG153 (pREG153 is a derivative of pREG151 [Weiss, A. et al. *J. Bact.* 152, 549–552] altered by substitution of ampicillin resistance for trimethoprin resistance and addition of λ cos sequences) and the "sticky" ends "filled in" as above. This fragment was then ligated to the vibrio DNA so that the Ap resistance gene was in exactly the same place as the now-deleted toxin genes, flanked by the same vibrio sequences. The resulting plasmid was designed pJBK21 (FIG. 4) containing the deletion toxin region and the Ap resistance gene.

EXAMPLE 2

Addition of Flanking Homogeneous Sequences, Followed by Conjugal Gene Transfer into *V. cholerae*

To insure the specific insertion into the chromosome of the deletion in pJBK21, approximately 7,000 bp of additional DNA was added to each end of the PstI-BglII fragment from pJBK21. (The probability of the homologous recombination event occurring increases with increasing length of flanking homologous sequences.) To achieve this, an approximately 18 kb fragment was cloned from the chromosome of N16961. This clone was designated pJBK44 and contains the 4 kb PstI-BglII tox gene fragment flanked by approximately 7kb of DNA on each side (see FIG. 5). The plasmid pJBK21 was partially digested with Pst I so that only one of the Pst sites would be cut (an additional Pst site was present within the ampicillin resistance gene) followed by digestion with Bgl II to isolate the 4 kb PstI-BglII fragment containing the deleted toxin region and the Ap resistance region. The plasmid pJBK44 containing the ca 18 kb vibrio fragment was partially digested with Bgl II so that only one of the 4 Bgl II sites present would be cut. This partial digestion was followed by complete digestion with Pst I and the resulting fragments separated by electrophoresis through 0.3% agarose. The separated fragments were then purified and analyzed and one fragment was found which contained all of the sequences of pJBK44 except for the 4 kb. PstI-BglII tox gene fragment (see FIG. 5.). This fragment representing the flanking DNA was then ligated to the Pst-Bgl fragment from pJBK21 containing the ampicillin resistance gene. The resulting plasmid, pJBK54, contained approximately 17 kb of Vibrio chromosome with an ampicillin resistance gene substituted for the deleted toxin genes.

The modified chromosomal region was the cloned into a plasmid which can be readily mobilized in *V. cholerae.* The plasmid pRK290 [Ditta, G. et al. *Proc. Nat. Acad. Sci.* 77, 7347 (1980)] belongs to the plasmid incompatibility group P and possesses a single Eco RI site into which pJBK54 was cloned (FIG. 6). The resulting plasmid pJBK55 was then mated into *V. cholerae* N16961 using the conjugative plasmid pRK2013, yielding *V. cholerae* N16961 (pJBK55) ($Ap^r$).

EXAMPLE 3

Recombination in vivo

The mutant toxin genes, after conjugal gene transfer as described in Example 2, now existed extrachromosomally in *V. cholerae* strain N16961 (see FIG. 1). At a very low frequency (perhaps $10^{-6}$ to $10^{-8}$) the homologous flanking sequences base pair and cross over into the chromosome (see FIG. 7). This rare event will result in the substitution of the deleted toxin region on the plasmid for the ctx genes on the chromosome. To select for this rare event, the plasmid incompatibility phenomenon was exploited [Ruvkin, G. B., supra]. Plasmids can be divided into incompatibility groups, designated A through W, on the basis of their ability to be stably maintained together in the same cell. If two plasmids cannot be stably maintained together in the same cell, they are incompatible and belong to the same incompatibility group presumably because they utilize the same replication mechanism in the cell. By selectively using an antibiotic resistance present on one plasmid but not on the other, it is possible to select which of two incompatible plasmids will be maintained. The plasmid pJBK55, because of its pRK290 origin, belongs to the (Inc) group P. The plasmid R702 also belongs to the Inc P group and encodes resistance to kanamycin, tetracycline, sulfonamide, and streptomycin, but not ampicillin. By mating pR702 ($Su^R$) into N16961 (pJBK55) ($Ap^R$) and selecting on media containing both ampicillin and sulfonamide, selection was made for cells in which the ampicillin resistance gene had been incorporated into the chromosome and the sulfonamide resistance marker remains on the plasmid R702, since pR702 and pJBK55 are incompatible (see FIG. 2). The resultant strain JBK56 (FIG. 3) was ampicillin resistant, and toxin negative when tested in Y-1 adrenal cells and by $Gm_1$ ELISA. Furthermore, when chromosomal DNA was hybridized to DNA probes containing cloned cholera toxin (CT) genes, JBK56 was negative, suggesting that the toxin genes were completely deleted.

The antibiotic resistance encoded on R702 was eliminated by selecting a spontaneously cured derivative lacking the plasmid (this occurred at a frequency of about 1 in 2,000).

EXAMPLE 4

Elimination of the Selectable Marker of Example 1

To eliminate the ampicillin resistance, a derivative of pJBK55 was constructed in which genes encoding resistance to mercury (Hg) from R100 were cloned into the Pst site of the Ap gene, thereby insertionally inactivating the ampicillin resistance gene. This derivative was then mated into *V. cholerae* JBK56, followed by pR702 and selection made as above for $Hg^R$, $Ap^S$ *V. cholerae.* The final strain, *V. cholerae* JBK70, is sensitive to all antibiotics tested, resistant to mercury, and phenotypically toxin negative. Its chromosomal DNA did not detectably hydridize to DNA probes containing CT genes. Short of sequencing the DNA for the entire chromosome, JBK70 appears to be unaltered from the parent strain N16961 except for the deletion of the toxin genes and insertion of mercury resistance and inactive ampicillin resistance genes. Such a strain cannot revert to toxigenicity because the toxin genes are not merely mutated but are completely deleted.

EXAMPLE 5

Conjugal Gene Transfer to Confer Antitoxic Immunity

If both antibacterial immunity and antitoxic immunity are desired for synergy, a derivative of JBK70 can be made to produce the B subunit of cholera toxin only. To accomplish this end, a toxin derivative was made that produces B only and lacks the genes for A (FIG. 8). A Hpa II fragment from pJBK16 containing the B structural gene was cloned into a phage cloning vector, M13mp7 placing a Bam HI and an Eco RI site on either side of the gene (FIG. 8). The fragment, now flanked by Bam HI sites was cloned into pMS 9 which contains the very strong trp promoter. The placing of the B genes under the transcriptional control of a strong promoter insures high production of B antigen. Of the clones examined, approximately 50% produced no antigen. This finding reflects the two possible orientations for the cloned insert—one forward, one backward. One derivative, pJBK51, which produced B subunit was mated into *Vibrio cholerae* JBK70 and found to produce even more B antigen than the parent strain N16961, yielding JBK70 (pJBK51). Other B-only mutants have been created using different promoters, including the P_L promoter and these can be evaluated in appropriate models for any significant in vivo expression differences.

EXAMPLE 6

Colonization of Infant Mouse Intestine with JBK70 without Reversion to Toxigenicity Suckling mice (2.0–3.5g.) were removed from their mothers and starved for 3 to 8 hours. Four of them were then inoculated on day 1 per os to stomach using a 22g animal feeding needle. The inoculum was about $10^8$ CFU (colony-forming units)/mouse of JBK70 in a volume of between 0.05 ml and 0.1 ml. The inoculum was prepared in BHI broth essentially as described in Baselski, V. et al, supra. The inoculum contained about 0.01% Evans blue dye. The presence of this dye in the stomach, seen through the abdominal wall, indicated proper delivery of the inoculum. Addition of Evans blue dye was discontinued after day 1 (see Table I), to avoid inhibition of JBK70.

Subsequent inoculations involved mouse-to-mouse (MXM), or alternatively, mouse-to-plate-to-mouse (MXPXM), but required different procedures to prepare the inoculum compared to the Baselski protocol for the inoculation on day 1.

To prepare MXM inoculum, the gut was dissected from stomach to anus under sterile precautions. The gut was weighed, placed in a glass homogenizer tube, and about 0.5 ml BHI broth added. The mixture was homogenized briefly with a Teflon pestle until tissue was liquified. The resulting suspension was used to inoculate about $10^{-8}$ CFU into each infant mouse. It was checked for purity by streaking on MEA (meat extract agar) plates. No Evans blue dye was added.

To prepare MXPXM inoculum, a sterile loop was used to transfer cells from an MEA plate to BHI broth. About $10^{11}$ CFU/ml were added to about 1 ml of BHI so that a dense suspension was formed. The mixture was vortexed to homogeneity, and 0.05-0.1 m. (about $10^{10}$ CFU) inoculated per os into each infant mouse. No evans blue dye was added.

For all inoculations, mice were held in beakers at room temperature of 73°–76° F. Beakers were placed in a plastic box which was loosely covered in order to maintain the mice at slightly above ambient temperature, about 78° F.

As the results in Table I indicated, there were sufficient cells in the intestine to inoculate the next animal, as checked by streaking on MEA plates. The *Vibrio cholerae* JBK70 therefore colonized the gut of infant mice. Furthermore, the fluid accumulation levels did not increase since there were no substantial increases in the FA ration (an FA ratio greater than or equal to 0.065 is a positive fluid accumulation). Evidence of reversion to toxigenicity would have indicated otherwise.

EXAMPLE 7

Construction of *V. cholerae* strain CVD101 having a Restriction Fragment Deletion within the Gene coding for the A Subunit Another classical strain chosen for attenuation was *Vibrio cholerae* Ogawa 395 (alternatively designated "395") which, like N16961, has been extensively studied in volunteers and confers solid immunity [Levine, M. M. "Immunity to cholera as evaluated in volunteers," in *Cholera and Related Diarrheas: 43rd Nobel Symposium*, Stockholm 1978. (O. Ouchterlong & J. Holmgren, eds.) Basel: S. Karger, pp. 195-2-3 (1980); Levine, M. M et al. *Acute Enteric*, supra (1981)]. The procedure employed in the attenuation of 395 was not substantially different from that employed for N16961 (as described in Examples 1–5).

Figure 9:
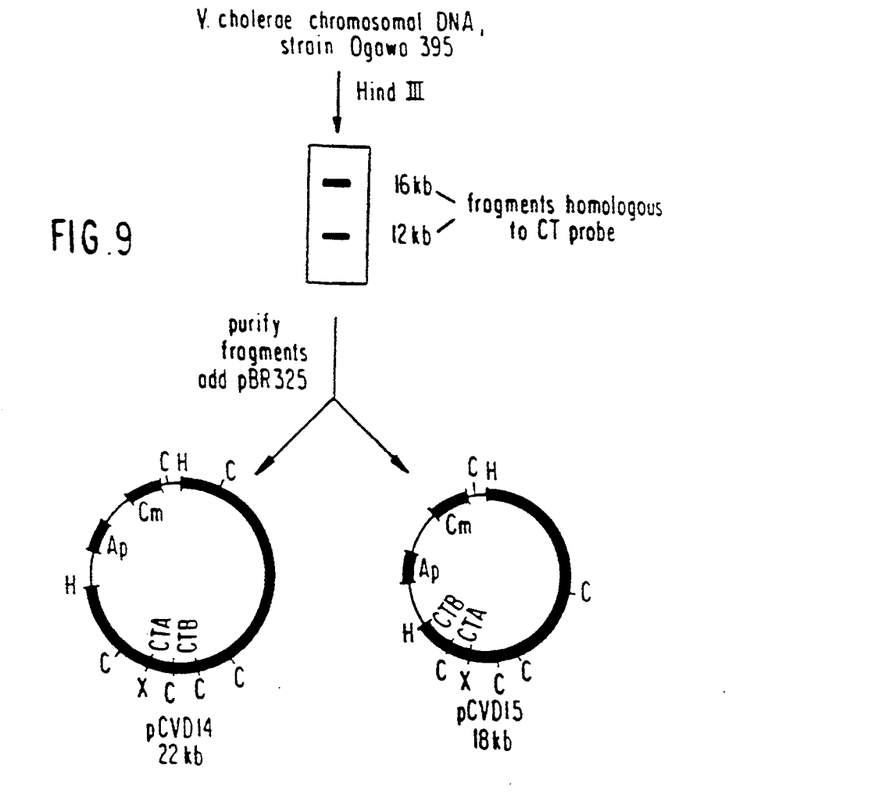
FIG. 9. Scheme for construction of pCVD14 and pCVD15.

The first step involved the cloning and mapping of the two toxin gene copies of 395. Southern blot analysis revealed two Hind III fragments of about 16 and about 12 kb in length, both of which hybridized with cloned cholera toxin genes. These fragments were purified by agarose gel electrophoresis and cloned into alkaline phosphatase treated-Hind III digested pBR325 (FIG. 9). The resulting recombinant plasmids containing the toxin genes were designated pCVD14 and pCVD15.

Figure 10:
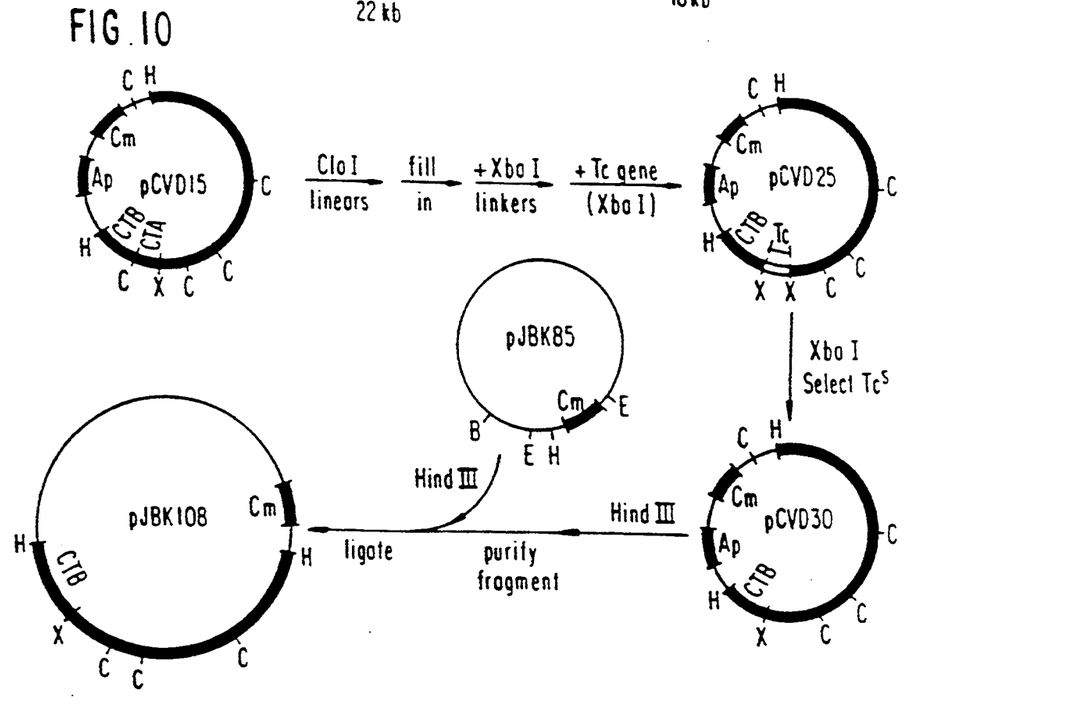
FIG. 10. Scheme for construction of pJBK108.

Plasmids pCVD14 and pCVD15 were then mapped with restriction endonucleases. An Xba I-Cla I fragment of about 550 bp was found, containing the entire base sequence of the $A_1$ subunit with the exception of codons for the first 10 amino acid residues of $A_1$. This Xba I-Cla I fragment was deleted in vitro from both pCVD14 and pCVD15 in a series of steps as shown in FIG. 10 for pCVD15. First, partial digestion with Cla I yielded a population of linear molecules in which only one of five Cla I sites was cut. Next, the ends of the linear molecules were made blunt-ended by filling in with DNA polymerase. Xba I linkers were ligated onto the blunt-ended Cla I sites yielding a collection of molecules in which an Xba I enzyme was then added to trim the linker and a tetracycline resistance gene on an Xba I fragment was added and ligated. After transformation into *E. coli* K-12 and selection on tetracycline, the plasmid content of a number of transformants was examined. A variety of deletion mutations were found in which one or more Xba I-Cla I fragments were deleted. One deletion mutant was chosen which lacked only the 550 bp Xba I-Cla I fragment containing the $A_1$ gene. This deletion mutant, designated pCVD25 was purified, digested with Xba I and religated to delete the tetracycline resistance gene. The resulting clone, PCVD30, was negative for holotoxin as measured in Y-1 adrenal assay [Sack, D. A. et. al. supra (1975)], but positive for production of B subunit, as measured by ELISA [Sack, D. A. et al. supra (1980)], and lacked the genes for $A_1$, as shown by DNA hydridization using labeled $A_1$ probe. The Hind III fragment of pCVD30 containing the toxin deletion mutation was then cloned into pJBK85, a Tc sensitive, Cm resistant derivative of pJBK108. The resulting plasmid was designated pJBK108.

Figure 11:
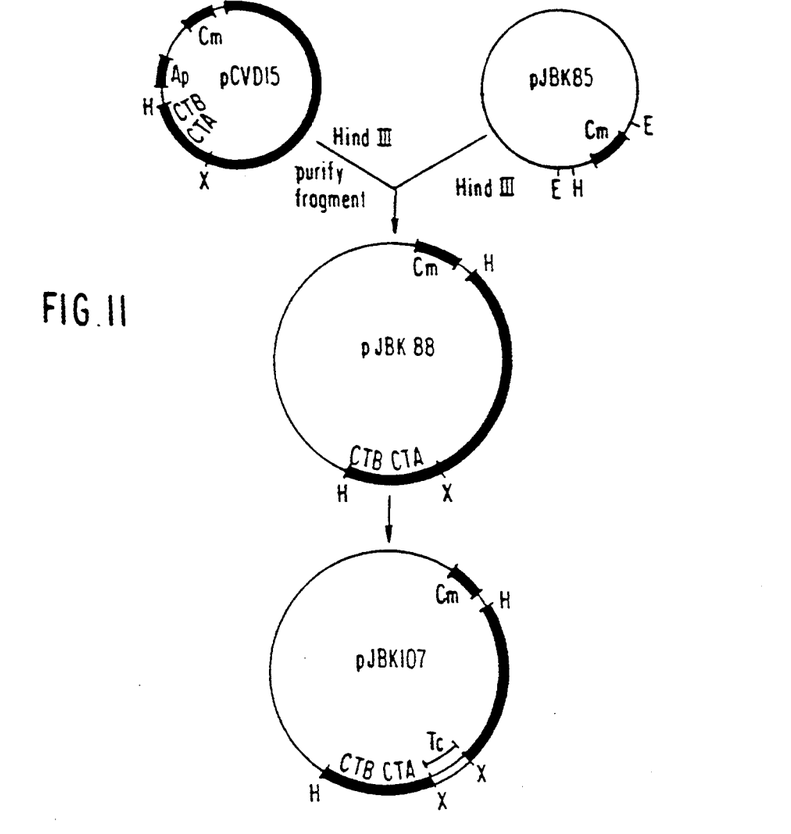
FIG. 11. Scheme for construction of pJBK107.

The lack of a selectable marker in the toxin deletion mutation in pJBK108 necessitated a modification of the method previously used to attenuate El Tor N16961. To accomplish the deletion of the $A_1$ genes from 395, the Hind III fragment from pCVD15 was cloned into pJBK85, resulting in pJBK88 (FIG. 11). The tetracycline resistance gene on a Xba I fragment was then cloned into the Xba site within the $A_1$ gene of PJBK88, yielding pJBK107. This tetracycline resistance was then recombined into the chromosome of 395 as previously done for *V. cholerae* pJBK56. pJBK107 (Tc$^r$, Cm$^r$) was mobilized into 395 and a second Inc P plasmid, pR751 (Tp$^r$) was introduced. Selection of Tc$^r$, Tp$^r$, Cm$^s$ colonies resulted in *V. cholerae* JBK113, which contained tetracycline resistance genes in both chromosomal toxin gene copies. pJBK108, containing the deletion mutation, was then mobilized into *V. cholerae* JBK113. Homologous recombination of the deletion mutation into the chromosome will result in the loss of the $A_1$ gene sequences, an event which can be detected by loss of tetracycline resistance. Because the recombination event occurs at a very low frequency, an enrichment procedure for tetracycline sensitive cells in a population of tetracycline resistant cells was employed. This enrichment procedure exploited the fact that tetracycline is a bacteriostatic antibiotic whereas ampicillin and D-cycloserine are bactericidal. Therefore, a culture of *V. cholerae* JBK 113 containing pJBK108 was grown for 3 hr at 37° in L-broth containing 2 micro g/ml tetracycline, 50 micro g/ml ampicillin and 50 micro g/ml D-cycloserine. At the end of 3 hours, most of the tetracycline resistant cells were killed, and tetracycline sensitive cells were detected by plating onto L-agar and replica plating onto L-agar with tetracycline. Tetracycline sensitive colonies were probed for the presence of $A_1$ genes by DNA hybridization. One tetracycline sensitive strain having deletions for both gene copies of the $A_1$ subunit was designated *V. cholerae* CVD101 and tested for production of B subunit by ELISA [Sack, supra]. *V. cholerae* CVD101 was found to produce B subunit antigen at levels substantially equivalent to the toxigenic parent *V. cholerae* 395.

EXAMPLE 8

DNA Sequencing of the Toxin Genes

Figure 12:
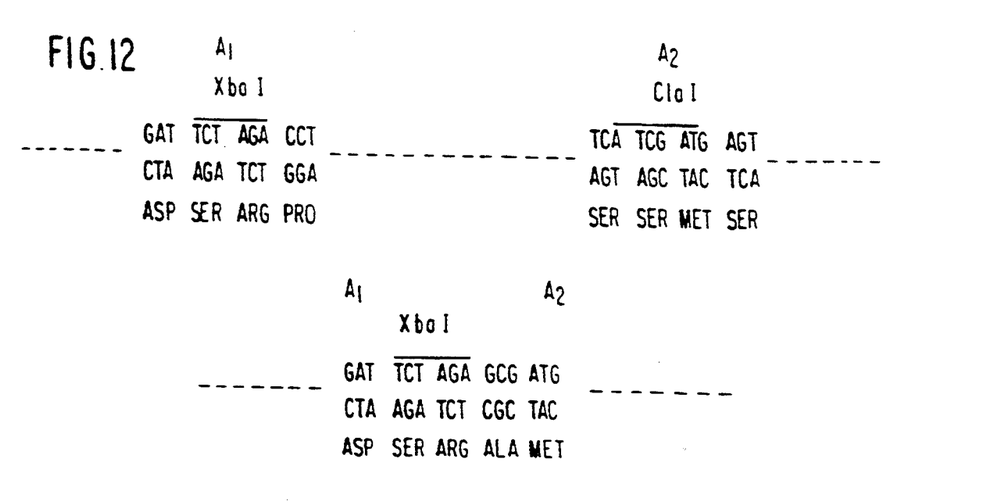
FIG. 12. DNA sequence of (top) the Xba I and Cla I sites, which determine the ends of the deleted Xba I-Cla I 550 bp fragment of the A subunit in Ogawa 395, and for (bottom) the junction in CVD101 after deletion of this fragment and insertion of an Xba I linker.

The entire DNA sequence of the toxin genes of *V. cholerae* Inaba 62746 has been determined, part of which has been reported in Lockman et al., *J. Biol. Chem.* 258, 13722 (1983). The restriction endonuclease mapping of pCVD14 and pCVD15 indicates that the sequences found in strain 62746 are also present in the toxin genes of 395. The predicted junction after deletion of the 550 bp Xba I-Cla I fragment, but with addition of an Xba I linker sequence, is shown in FIG. 12. The Xba I site of the cholerae toxin sequence spans amino acid residues 10 and 11 of the $A_1$ structural gene (not counting the 18 amino acid leader sequence for $A_1$). The Cla I site of the sequence is located at the last residue of $A_1$ and the first residue of $A_2$.

EXAMPLE 9

Construction of *V. Cholera* CVD103

Another classical strain chosen for attenuation was *V. cholerae* Inaba 569B (alternatively designated "569B"). The procedure employed in the attenuation of 569B was not substantially different from that employed for 395. The procedure used to prepare CVD103 is the same as to prepare CVD101, except that 569B was used rather than 395.

A 550 bp Xba I-Cla restriction fragment encoding 94% of the $A_1$ peptide was deleted in vitro from the cloned cholera toxin genes. This mutation was then recombined into the chromosome of 569B and replaced the active toxin gene sequence of this strain. (As in CVD101, two cholera toxin gene copies were replaced in the parent strain. Vaccine strain *V. cholerae* JBK70 had only a single cholera toxin gene copy).

The resulting strain, CVD103, has demonstrated its ability to confer protective immunity with a minimum of reactogenicity. It is clinically well tolerated, yet immunogenic and protective. Levine et al., *Lancet*, pgs. 467–470 (August 1988), which is incorporated herein by reference, reports challenge studies after vaccination by CVD103 and reports vaccine efficacy of 87%, 82% and 67% for different challenge strains at page 467, Table II, and lines 8 to 21. CVD103 caused only mild diarrhea in 6 of 52 volunteers and these vaccinees did not suffer from the syndrome of abdominal cramps, malaise, headache and nausea that had been seen in approximately one-half of the recipients of other vaccine strains, including JBK70, CVD101, and strain 395N1 disclosed in U.S. Pat. No. 4,882,278 (Mekalanos). *Vibrio cholerae* strain CVD103Hg$^r$ has been deposited with the American Type Culture Collection and been given ATCC designation number 55456.

EXAMPLE 10

Construction of CVD103Hg$^r$

CVD103Hg$^r$ is a derivative of CVD103. This strain contains a mercury resistance marker. The mercury resistance marker allows the strain to be distinguished from other strains of *Vibrio cholerae* which could conceivably co-infect a recipient of the vaccine in a cholera-endemic area such as Bangladesh or India. By inoculating a plate of agar medium containing mercuric chloride, CVD103Hg$^r$ is distinguished from other strains by its ability to grow on mercury versus the growth inhibition seen with other strains on this medium. To construct CVD103Hg$^r$, the genes encoding the hemolysin of *V. cholerae* (the hly genes) were first cloned into *E. coli*. The hly sequences were digested with the restriction enzyme HpaI and a 4.2 kilobase fragment encoding mercury resistance originally derived from the plasmid R100 was cloned into the HpaI site. Mutation of the hly gene at the HpaI site does not interfere with the colonization and immunizing ability of *V. cholerae*. (Kaper, et al., Advances in Research on Cholera and Related Diarrheas, vol. 6, Y. Takeda and R. B. Sack, editors, KTK Scientific Publishers, Tokyo, 1988, pps. 161–167.) The construction, i.e., the cloned hly genes with the inserted mercury resistance gene, was then mobilized into *V. cholerae* CVD103. Once inside the bacterial cell, the mutated hly sequences recombined with the homologous sequences in the CVD103 chromosome, and resulted in the incorporation of the mercury resistance gene in the chromosome of CVD103. The resulting strain was designated CVD103Hg$^r$.

CVD103Hg$^r$ has demonstrated its ability to provide significant protection in challenge studies, and is even better tolerated than CVD103 (Levine et al., *The Lancet*, "Safety, Immunogenicity, And Efficacy Of Recombinant Live Oral Cholera Vaccines, CVD 103 and CVD103Hgr", Aug. 27, 1988, pps 467–470.) CVD103Hg$^r$ has been well-tolerated in randomized, double-blind, placebo-controlled studies carried out in Swiss adults. Cryz et al., *Vaccine* 8, pgs. 577–579 (December 1990). Besides being well-tolerated, CVD103Hg$^r$ exhibits a high degree of protective efficacy. The best immunologic correlate of protection is seroconversion of vibriocidal antibody. In North American studies, 95% of subjects who received CVD103Hg$^r$ vaccine mounted a $\geq$ fourfold rise in Inaba vibrocidal antibody titre (Levine et al., supra), and a response rate of 88% was seen in Swiss subjects (Cryz et al., *Vaccine* 8, at page 579). Thus, the high rate of seroconversion and the good titres of both Inaba and Ogawa vibriocidal antibody achieved after administration of a single dose of CVD103Hg$^r$ suggest that a high level of protection may be conferred by immunization with the dosage tested. Indeed, studies involving volunteers immunized with a single dose of CVD103Hg$^r$ show that they were significantly protected against experimental challenge with classical biotype *V. cholerae* of either Inaba or Ogawa serotype and against El Tor Inaba.

Experimental studies that have been carried out to assess the protective efficacy of CVD103Hg$^r$ have used the following pathogenic strains as challenge organisms: classical Inaba 569B; El Tor Inaba N16961; El Tor Ogawa E7946. CVD103Hg$^r$ has provided significant protection against diarrhea due to all of these challenge strains of different biotypes and serotypes. Moreover, protection was 100% against severe cholera (diarrheal purge of $\geq 5.0$ liters) and against moderate cholera (diarrheal purge of $\geq 3.0$ liters). Overall protection against any diarrhea ($\geq 2.0$ liters of loose stools) was 100% against the classical challenge strain and 60% against El Tor challenge strains. Applicants have carried out extensive clinical studies with CVD103Hg$^r$ in healthy adults in the U.S.A., in Switzerland, and in Thailand and in children in Indonesia.

While the invention has been described in connection with specific embodiments thereof, it will be understood that it is capable of further modification and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. *Vibrio cholerae* CVD103Hg$^r$ (ATCC No. 55456).

2. A culture of *Vibrio cholerae* comprising *Vibrio cholerae* CVD103Hg$^r$ (ATCC No. 55456).

3. A method of isolating deletion mutants of *Vibrio cholerae* Inaba comprising the steps of:
   (a) constructing a first plasmid comprising *Vibrio cholerae* flanking sequences of the coding sequence for the A$_1$ subunit of *Vibrio cholerae* toxin and a gene for a first selectable marker of foreign origin ligated to said flanking sequences or coding sequence, wherein said flanking sequences are of sufficient length to promote detectable in vivo recombination;
   (b) mating virulent strain 569B of *Vibrio cholerae* with a first microorganism carrying the first plasmid;
   (c) selecting for *Vibrio cholerae* expressing the first selectable marker;
   (d) mating the selected product of step (c) with a second microorganism carrying a second plasmid with a second selectable marker, said second plasmid being incompatible with the first plasmid in said second microorganism;
   (e) selecting for *Vibrio cholerae* expressing both the first selectable marker and the second selectable marker to isolate an in vivo recombinant *Vibrio cholerae* organism;
   (f) mating said in vivo recombinant *Vibrio cholerae* with a third microorganism carrying a third plasmid, said third plasmid comprising flanking sequences of the coding sequence for the A$_1$ subunit of *Vibrio cholerae* toxin, said coding sequence comprising a deleted fragment of sequence;
   (g) selecting for the loss of the first selectable marker;
   (h) mating the selected product of step (g) with a fourth microorganism carrying a fourth plasmid, said fourth plasmid encoding a gene conferring a resistance to mercury; and,
   (i) selecting for *Vibrio cholerae* expressing the gene conferring resistance to mercury.

4. The method according to claim 3 wherein said first, second, third and fourth microorganisms are *E. coli* strains.

5. The method according to claim 3 wherein said first and second selectable markers are antibiotic resistance genes.

6. The method according to claim 3 wherein said gene conferring resistance to mercury in step (i) is incorporated into the hemolysin gene of 569B.

7. The method according to claim 6 wherein said *Vibrio cholerae* in step (i) is CVD103Hg$^r$ (ATCC No. 55456).

8. A *Vibrio cholerae* having substantially all of the identifying characteristics of CVD103Hg$^r$ (ATCC No. 55456).

* * * * *